United States Patent [19]

Rasmusson et al.

[11] Patent Number: 5,571,817

[45] Date of Patent: Nov. 5, 1996

[54] METHODS OF TREATING ANDROGENIC ALOPECIA WITH FINASTERIDE [17β-N-MONO-SUBSTITUTED-CARBAMOYL-4-AZA-5-α-ANDROST-1-EN-ONES]

[75] Inventors: Gary H. Rasmusson, Watchung; Glenn F. Reynolds, Westfield, both of N.J.

[73] Assignee: Merck & Co., Inc., Rahway, N.J.

[21] Appl. No.: 94,815

[22] Filed: Jul. 20, 1993

Related U.S. Application Data

[63] Continuation of Ser. No. 16,476, Feb. 10, 1993, abandoned, which is a continuation of Ser. No. 927,256, Aug. 7, 1992, abandoned, which is a continuation of Ser. No. 698,374, May 9, 1991, abandoned, which is a continuation of Ser. No. 545,676, Jun. 28, 1990, abandoned, which is a continuation of Ser. No. 370,142, Jun. 21, 1989, abandoned, which is a continuation of Ser. No. 198,708, May 19, 1988, abandoned, which is a continuation of Ser. No. 34,806, Apr. 3, 1987, abandoned, which is a continuation-in-part of Ser. No. 800,623, Nov. 21, 1985, Pat. No. 4,760,071, which is a continuation of Ser. No. 584,062, Feb. 27, 1984, abandoned.

[51] Int. Cl.⁶ ................................. A61K 31/44
[52] U.S. Cl. ............................. 514/284; 546/77
[58] Field of Search ..................... 546/77; 514/284

[56] References Cited

U.S. PATENT DOCUMENTS

| | | | |
|---|---|---|---|
| 2,227,876 | 1/1941 | Bolt | 260/269 |
| 3,239,417 | 3/1966 | Tullio et al. | 167/65 |
| 3,264,301 | 8/1966 | Doorenbos et al. | 260/286 |
| 3,285,918 | 11/1966 | Doorenbos et al. | 260/251 |
| 4,139,619 | 2/1979 | Chidsey, III | 424/45 |
| 4,220,775 | 9/1980 | Rasmusson et al. | 546/77 |
| 4,317,817 | 3/1982 | Blohm et al. | 424/226 |
| 4,377,584 | 3/1983 | Rasmusson et al. | 424/258 |
| 4,396,615 | 8/1983 | Petrow et al. | 424/242 |
| 4,596,812 | 6/1986 | Chidsey, III et al. | 514/256 |
| 4,689,345 | 8/1987 | Kasha et al. | 514/546 |
| 4,732,897 | 3/1988 | Cainelli et al. | 514/222 |
| 4,760,071 | 7/1988 | Rasmusson et al. | 514/284 |
| 4,845,104 | 7/1989 | Carlin et al. | 514/284 |
| 4,859,681 | 8/1989 | Rasmusson et al. | 514/284 |
| 4,882,319 | 11/1989 | Holt et al. | 514/119 |
| 4,888,336 | 12/1989 | Holt et al. | 514/278 |
| 4,910,226 | 3/1990 | Holt et al. | 514/573 |
| 5,021,575 | 6/1991 | King et al. | 546/77 |
| 5,049,562 | 9/1991 | Rasmusson et al. | 514/284 |
| 5,061,802 | 10/1991 | Steinberg et al. | 546/77 |
| 5,075,450 | 12/1991 | Rasmusson et al. | 546/285 |
| 5,084,574 | 1/1992 | Bhattacharya et al. | 546/77 |
| 5,091,380 | 2/1992 | Rasmusson et al. | 514/169 |
| 5,120,729 | 6/1992 | Chabala et al. | 514/210 |
| 5,120,742 | 6/1992 | Rasmusson et al. | 514/284 |

(List continued on next page.)

FOREIGN PATENT DOCUMENTS

| | | |
|---|---|---|
| 970692 | 7/1975 | Canada . |
| 0004949 | 10/1979 | European Pat. Off. . |
| 0155096 | 9/1985 | European Pat. Off. . |
| 0277002 | 8/1988 | European Pat. Off. . |
| 0289327 | 11/1988 | European Pat. Off. . |
| 0314199 | 5/1989 | European Pat. Off. . |
| 0343954 | 11/1989 | European Pat. Off. . |
| 0375347 | 6/1990 | European Pat. Off. . |
| 0375349 | 6/1990 | European Pat. Off. . |
| 0375345 | 6/1990 | European Pat. Off. . |
| 0375344 | 6/1990 | European Pat. Off. . |
| 0463638 | 1/1992 | European Pat. Off. . |
| 1465544 | 11/1965 | France . |
| 59-13719 | 1/1984 | Japan . |
| 60-116657 | 6/1985 | Japan . |
| 60-126218 | 7/1988 | Japan . |
| 83/7859 | 11/1984 | South Africa . |
| WO85/05272 | 12/1985 | WIPO . |
| WO85/05270 | 12/1985 | WIPO . |

OTHER PUBLICATIONS

Orentreich, Ann. Plast. Surg. (United States), Jan. 1978, pp. 116–118, "Medical treatment of baldness".

Questel. Orbit, JAPIO file (abstract), accession No. 84–013719 (1984).

Derwent WPAT file (abstract), accession No. 85–200306/33 (1985).

Questel. Orbit, JAPIO file (abstract), accession No. 85–116657 (1985).

Neri, et al., "A Biological Profile of Nonsteroidal Antiandrogen, SCH 13521", Endo., vol. 91, No. 2, pp. 427–437 (1972).

Nayfeh, et al., "Metabolism of Progesterone by Rat Testicular Homogenates", Steroids, vol. 14, pp. 269–283 (1969).

Voigt, et al., Endo., vol. 92, p. 1216.

Doorenbos, et al., "Synthesis and Antimicrobial Properties of 17 Beta–Isopentyloxy . . . ", J. Pharm. Sci., vol. 62, No. 4 pp. 638–640 (1973).

Doorenbos, et al., "4–17 Alpha–Dimethyl–4–Aza–5 Alpha–Androstan–17 Beta–ol–Acetate . . . ", J. Pharm. Sci., vol. 60, No. 8, pp. 1234–1235 (1971).

(List continued on next page.)

*Primary Examiner*—Peter O'Sullivan
*Attorney, Agent, or Firm*—Carol S. Quagliato; Melvin Winokur; Robert J. North

[57] ABSTRACT

17β-N-monosubstituted-carbamoyl-4-5α-androst-1-en-3-ones of the formula

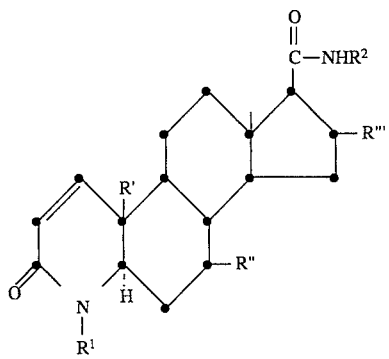

wherein $R^1$ is selected from hydrogen, methyl and ethyl and $R^2$ is a branched chain alkyl of from 3–12 carbons, and R', R", R'" are hydrogen or methyl are active as testosterone 5α-reductase inhibitors and thus are useful topically for treatment of androgenic alopecia.

2 Claims, No Drawings

U.S. PATENT DOCUMENTS

| | | | |
|---|---|---|---|
| 5,138,063 | 8/1992 | Rasmusson et al. | 546/77 |
| 5,151,429 | 9/1992 | Rasmusson et al. | 514/284 |
| 5,151,430 | 9/1992 | Steinberg et al. | 514/284 |
| 5,162,332 | 11/1992 | Steinberg et al. | 514/284 |
| 5,175,155 | 12/1992 | Juniewicz et al. | 514/176 |
| 5,196,411 | 3/1993 | Rasmusson et al. | 514/169 |

OTHER PUBLICATIONS

Doorenbos, et al., "Synthesis and Evaluation of Antimicrobial Properties . . . ", J. Pharm. Sci., vol. 63, No. 4, pp. 620–622 (1974).

Back, et al., "N–Chloroazasteroids: A Novel Class of Reactive Steroid Analogues", J. Org. Chem., vol. 54, pp. 1904–1910 (1989).

Liang, et al., "Inhibition of 5 Alpha–Reductase, Receptor Binding and Nuclear Uptake of Androgens . . . ", Chem. Abs., vol. 95, No. 13, p. 99, AB #109055j (1981).

Brooks, et al., "Prostatic Effects Induced in Dogs by Chronic or Acute Oral Administration . . . ", The Prostate, vol. 9, pp. 65–75 (1986).

Kadohama, et al., "Retardation of Prostate Tumor Progression in Nobel Rat . . .", J NCI, vol. 74, No. 2, pp. 475–486 (1985).

Andriole, et al., "The Effect of 4MA, a Potent Inhibitor of 5 Alpha–Reductase . . . ", The Prostate, vol. 10, pp. 189–197 (1987).

Bingham, et al., "The Metabolism of Testosterone By Human Male Scalp Skin", J. Endocr. (England), vol. 57, pp. 111–121 (1973).

Kedderis, et al., "Studies with Nitrogen–Containing Steroids and Freshly Isolated Rat Hepatocytes", Tox. Appl. Pharm., vol. 93, pp. 403–412 (1988).

Liang, et al. "Species Differences in Prostatic Steroid 5–Alpha Reductases . . . ", Endocrinology, vol. 117, pp. 571–579 (1985).

Stone, et al., "Estrogen Formation in Human Prostatic Tissue from Patients . . .", The Prostate, vol. 9, pp. 311–318 (1986).

Brooks, et al., "5 Alpha Reductase Inhibitory and Anti–Androgenic Activities . . . ", Steroids, vol. 47, pp. 1–19 (1986).

Labrie, et al., "Combination Therapy in Prostate Cancer", Lancet, vol. 2, #8515, pp. 1095–1096 (1986).

Rasmusson, et al., "Azasteroids: Structure–Activity Relationships for Inhibition . . . ", J. Med. Chem., vol. 29, pp. 2298–2315 (1986).

Rasmusson, et al., "Azasteroids as Inhibitors of Rat Prostatic 5–Alpha Reductase", J. Med. Chem., vol. 27, pp. 1690–1701 (1984).

Rittmaster, et al., "The Effects of N,N–Diethyl–4–Methyl–3–Oxo–4–Aza–5–Alpha Androstane . . . " J. Clin. Endo. & Metab., vol. 65, pp. 188–193 (1987).

Metcalf, et al., "Potent Inhibition of Human Steroid 5 Alpha–Reductase . . . ", Bioorganic Chem., vol. 17, pp. 372–376 (1986).

Levy, et al., "Inhibition of Rat Liver Steroid 5 Alpha–Reductase by 3–Androstene . . . ", Biochemistry, vol. 29, pp. 2815–2824 (1990).

Holt, et al., "Steroidal A Ring Aryl Carboxylic Acids . . . ", J. Med. Ch vol. 33, pp. 937–942 (1990).

Levy, et al., "Interaction Between Rat Prostatic Steroid 5 Alpha Reductase . . . ", J. Steroid Biochem, vol., 34, pp. 571–575 (1989).

Holt, et al., "Inhibition of Steroid 5 Alpha–Reductase by Unsaturated.", J. Med. Chem., vol. 33, pp. 943–950 (1990).

Metcalf, et al., "Inhibitors of Steroid 5 Alpha Reductase in Benign . . . ", TIPS, vol. 10, pp. 491–495 (1989).

Murphy, et al., "The Effect of Estradiol on a 25–Hydroxycholecalciferol Binding Protein . . . ", Steroids, vol. 35, pp. 1–7 (1980).

Diani, et al., "Hair Growth Effects of Oral Administration of Finasteride, a Steroid . . . ", J. Clin. Endo. & Metab., vol. 74, pp. 345–350 (1992).

Presti, Jr., et al., "Multicenter, Randomized, Double–Blind, Placebo Controlled Study . . . ", J. Urology.

Gormley, et al., "A Placebo Controlled Study of Finasteride (MK–906) on Stage D Prostate Cancer", Abst. of talk at Amer. Urol. Assoc. Mtg. in Canada (1991).

Gormley, et al., "Role of 5 Alpha Reductase Inhibitors in Treatment of Advanced Prostatic Carcinoma", Urol. Clinics of N. Amer., vol. 18, pp. 93–98 (1991).

Gormley, et al., "Effect of Finasteride on Serum PSA Levels in Men w/Prostate Cancer", 2nd Intnl. (Jan. 18, 1992).

Huggins, et al., "Studies on Prostatic Cancer", Cancer Research, pp. 293–297 (1941).

Rainwater, et al., "Prostate–Specific Antigen Testing in Untreated & Treated . . . ", Mayo Clinic Proc., vol. 65, pp. 1118–1126 (1990).

Arai, et al., "Prognostic Significance of Prostate Specific Antigen in Endocrine . . . ", J. of Urol., vol. 144, pp. 1415–1419 (1990).

Hudson, et al., "Clinical Use of Prostate Specific Antigen in Patients with Prostate Cancer", J. of Urol., vol. 142, pp. 1011–1017 (1989).

Brawer, et al., "Prostate–Specific Antigen in Management of Prostatic Carcinoma", Supp. to Urology, vol. 33, pp. 11–16 (1989).

Stamey, et al., "Prostate–Specific Antigen as a Serum Marker for Adenocarcinoma . . . ", N. E. Jour. Med., vol. 317, pp. 909–916 (1987).

Walsh, et al., "The Value of Prostate–Specific Antigen in the Management . . . ", Ther. Prog. Urol. Can., pp. 27–33 (1989).

Stamey, et al., "Prostate Specific Antigen in the Diagnosis and Treatment of Adenocarcinoma . . . ", J. of Urology, vol. 141, pp. 1070–1075 (1989).

Lange, et al., "The Value of Serum Prostate Specific Antigen Determinations . . . ", J. of Urol., vol. 141, pp. 873–879 (1989).

Hoehn, et al., "Human Prostatic Adenocarcinoma", The Prostate I, pp. 95–104 (1980).

Helliker, "Alopecia Sufferers Seek to Suffer Less . . . ", Wall Street Journal pp. A1–A7 (1991).

Chemical Engineering News, pp. 7–8 (29 Jun. 1992).

Allen & Hanburys Limited (Hayes') Appl (1977) RPC 113.

Television Transcript, News 4 New York Live at Five, WNBC–TV, NY, S. Simmons and M. Gomez (Nov. 29, 1993).

METHODS OF TREATING ANDROGENIC ALOPECIA WITH FINASTERIDE [17β-N-MONO-SUBSTITUTED-CARBAMOYL-4-AZA-5-α-ANDROST-1-EN-ONES]

The instant application is a continuation of Ser. No. 08/016,476, filed Feb. 10, 1993, now abandoned; which was a continuation of Ser. No. 07/927,256, filed Aug. 7, 1992, now abandoned; which was a continuation of Ser. No. 07/698,374, filed May 5, 1991, now abandoned; which was a continuation of Ser. No. 07/545,676, filed Jun. 28, 1990, now abandoned; which was a continuation of Ser. No. 07/370,142, filed Jun. 21, 1989, now abandoned; which was a continuation of Ser. No. 07/198,708, filed May 19, 1988, now abandoned; which was a continuation of Ser. No. 07/034,806, filed Apr. 3, 1987, now abandoned; which was a continuation-in-part of Ser. No. 06/800,623, filed Nov. 21, 1985 now U.S. Pat. No. 4,760,071; which was a continuation of Ser. No. 06/584,062, filed Feb. 27, 1984, now abandoned.

BACKGROUND OF THE INVENTION

The present invention is concerned with novel 17β-N-monosubstituted-carbamoyl-4-aza-5α-androst-1-ene-3-one compounds and the use of such compounds as testosterone-5α-reductase inhibitors for the treatment of androgenic alopecia, including male pattern alopecia.

DESCRIPTION OF THE PRIOR ART

It is well known in the art that certain undesirable physiological manifestations, such as acne vulgaris, seborrhea, female hirsutism, male pattern baldness and benign prostatic hypertrophy, are the result of hyperandrogenic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal anti-androgens have also been developed, for example, 4'-nitro-3'-trifluoromethylisobutyranilide. See Neri et al., Endo., Vol. 91, No. 2 (1972). However, these products, though devoid of hormonal effects, are peripherally active, competing with the natural androgens for receptor sites, and hence have a tendency to feminize a male host or the male fetus of a female host.

It more recently became known in the art that the principal mediator of androgenic activity in some target organs is 5α-dihydrotestosterone, and that it is formed locally in the target organ by the action of testosterone-5α-reductase. It therefore has been postulated and demonstrated that inhibitors of testosterone-5α-reductase will serve to prevent or lessen symptoms of hyperandrogenic stimulation. Nayfe et al., Steroids, 14, 269 (1969) demonstrated in vitro that methyl 4-androsten-3-one-17β-carboxylate was a testosterone-5α-reductase inhibitor. Then Voigt and Hsia, Endocrinology, 92, 1216 (1973), Canadian Pat. No. 970,692, demonstrated that the above ester and the parent free acid, 4-androsten-3-one-17β-carboxylic acid are both active inhibitors of testosterone-5α-reductase in vitro. They further demonstrated that topical application of either testosterone or 5α-dihydrotesterone caused enlargement of the female hamster flank organ, an androgen dependent sebaceous structure. However, concomitant administration of 4-androsten-3-one-17β-carboxylic acid or its methyl ester inhibited the response elicited by testosterone but did not inhibit the response elicited by 5α-dihydrotestosterone. These results were interpreted as indicating that the compounds were antiandrogenic by virtue of their ability to inhibit testosterone-5α-reductase.

A number of 4-aza steroid compounds are known. See, for example, U.S. Pat. Nos. 2,227,876; 3,239,417; 3,264,301; and 3,285,918; French Pat. No. 1,465,544; Doorenbos and Solomons, J. Pharm. Sci. 62, 4, pp. 638–640 (1973); Doorenbos and Brown, J. Pharm. Sci., 60 8, pp. 1234–1235 (1971); and Doorenbos and Kim, J. Pharm. Sci. 63, 4, pp. 620–622 (1974).

In addition U.S. Pat. No. 4,377,584 and 4,220,775 of Rasmusson et al. describe a group of 4-aza-17β-substituted-5α-androstan-3-ones which are said to be useful in the treatment of hyperandrogenic conditions. However, none of the cited references suggest that any of the novel 17βN-(monosubstituted) carbamoyl-4-aza-5α-androst-1-en-3-ones of the present invention would have utility as highly potent testosterone-5α-reductase inhibitors.

DESCRIPTION OF THE INVENTION

The present invention is concerned with novel 17β-N-(monosubstituted)-carbamoyl-4-aza-5α-androsten-1-en-3-one compounds, processes for their preparation, pharmaceutical formulations comprising the novel compounds as active ingredients and methods of inhibiting testosterone-5α-reductase and of treating androgen sensitive conditions with the novel compounds or their pharmaceutical formulations.

The present invention is concerned with compounds of the formula:

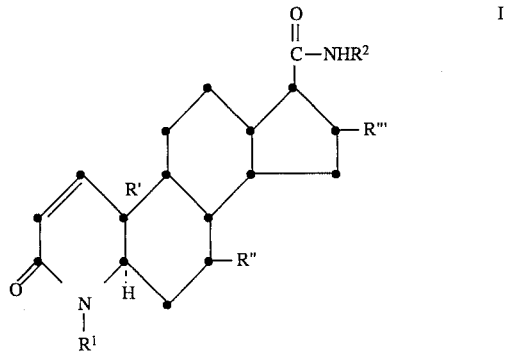

wherein $R^1$ is hydrogen, methyl or ethyl.

$R^2$ is a hydrocarbon radical selected from straight and branched chain alkyl of from 1–12 carbons or monocyclic aryl optionally containing 1 or more lower alkyl substituents of from 1–2 carbon atoms and/or 1 or more halogen (Cl, F or Br) substituents.

R' is hydrogen or methyl.

R" is hydrogen or β-methyl.

R''' is hydrogen, α-methyl or β-methyl.

A preferred embodiment of the novel compounds of our invention is represented by the formula:

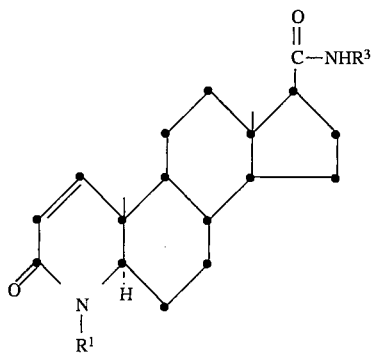

wherein $R^1$ is hydrogen, methyl or ethyl, and $R^3$ is branched chain alkyl of from 4–8 carbons.

Representative compounds of the present invention include the following:

17β-(N-tertbutylcarbomoyl)-4-aza-4-methyl-5-α-androst-1-en-3-one,

17β-(N-isobutylcarbamoyl)-4-aza-4-methyl-5-α-androst-1-en-3-one,

17β-(N-tert-octylcarbomoyl)-4-aza-4-methyl-5α-androst-1-en-3-one,

17β-(N-octylcarbamoyl)-4-aza-4-methyl-5α-androst-1-en-3-one,

17β-(n-1,1-diethylbutylcarbamoyl)-4-aza-4-methyl-5-α-androst-1-en-3-one,

17β-(N-neopentylcarbamoyl)-4-aza-4-methyl-5α-androst-1-en-3-one,

17β-(N-tert-amylcarbamoyl)-4-aza-4-methyl-5α-androst-1-en-3-one,

17β-(N-tert-hexylcarbamoyl)-4-aza-4-methyl-5α-androst-1-en-3-one.

and the corresponding compounds wherein the 4-methyl substituent is replaced in each of the above named compounds by a hydrogen or an ethyl radical.

Also included as representative compounds are any of the above indicated compounds having the N-branched chain alkyl substituent replaced by a methyl, ethyl, propyl, i-propyl, butyl, phenyl; 2, 3 or 4 tolyl, xylyl, 2-bromo or 2-chlorophenyl, 2-6-dichloro, or a 2,6-dibromophenyl substituent.

The novel compounds of formula I of the present invention are prepared by a method starting with the known steroid ester of the formula:

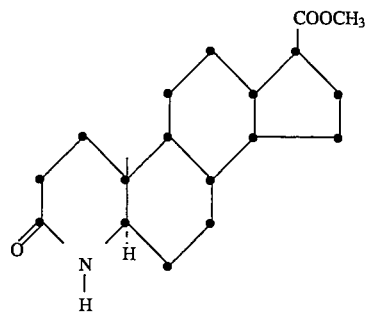

17β-(carbomethoxy)-4-aza-5-α-androstan-3-one which includes the stages of 1) dehydrogenating said starting material to produce the corresponding compound containing a double-bond in the 1,2-position of the A-ring, 2) converting the 17-carbomethoxy substituent into an N-monosubstituted carbamoyl substituent and, if desired, 3) alkylating the A-ring nitrogen to introduce a N-methyl or 4-ethyl substituent into the A ring. In carrying out the process of the present invention, it is essential that Stage 1 dehydrogenation of the 1,2-position of the steroid A ring be carried out using a 4-aza-5α-androstane-3-one-compound having no substituent other than hydrogen attached to the A-ring nitrogen. Stage 2 may consist of one or more chemical steps and if desired may take place before stage (1) or following stage (1) or stage (3).

In accordance with the process of the present invention, the products of our invention are formed by 1) heating a 17β-alkoxycarbonyl-4-aza-5α-androstan-3-one compound III with a dehydrogenating agent such as benzeneselenic anhydride in refluxing chlorobenzene to form a 17β-alkoxycarbonyl-4-aza-5α-androst-1-ene-3-one IV, 2) the formed 5α-androst-1-en-3-one compound from Step 1 is reacted with sodium hydride under anhydrous conditions in a neutral solvent such as dimethylformamide, 3) contacting the resulting reaction mixture with an alkyl (methyl or ethyl) iodide to form the corresponding 17-β-alkoxy-carbamoyl-4-alkyl-4-aza-5α-androst-1-en-3-one V, 4) subsequently hydrolyzing said 17β-alkoxycarbonyl-4-alkyl-4-aza-5α-androst-1-en-3-one with a strong base such as aqueous methanolic potassium hydroxide at the reflux temperature, followed by acidification and isolation of the resulting steroidal acid, 17β-carboxy 4-alkyl-4-aza-5α-androst-1-en-3-one VI, 5) said steroidal acid is then converted to its corresponding 2-pyridylthio ester by refluxing with triphenyl phosphine and 2,2'-dipyridyl disulfide in an inert solvent such as toluene and the resulting product 17β-(2-pyridylthiocarbonyl)-4-alkyl-4-aza-5α-androst-1-en-3-one VII is isolated by chromatography on silica gel, 6) said pyridylthio ester is then reacted with ethyl amine in tetrahydrofuran to form the desired products 17β-N-ethylcarbamoyl-4-alkyl-4-aza-5α-androst-1-en-3-one VIII which is isolated by chromatography on silica gel. When the previous reaction is carried out using an amine of formula $R^2NH$ in place of ethyl amine, the corresponding 17β-(N-$R^2$-carbamoyl)-4-alkyl-4-aza-5α-androst-1-en-3-one is prepared.

In accordance with the process of our invention the corresponding 17β(N-$R^2$-carbamoyl)-4-aza-5α-androst-1-en-3-one XIV is readily prepared from the 17β(alkoxycarbonyl)-4-aza-5α-androstone-3-one IV by repeating the above series of reaction steps but omitting Step 2 herein above i.e. treatment of the 4-aza-5-α-androst-1-en-3-one with sodium amide followed by methyl or ethyl iodide via intermediates XII and XIII.

In accordance with a further alternate process of preparing the compounds of our invention having only hydrogen as the sole substituent on the ring A—nitrogen, the double bond in the A ring is introduced as the last step of the process. Thus, a 17β-alkoxycarbonyl 4-aza-5α-androstan-3-one III is hydrolyzed to the corresponding steroidal acid IX 17β-carboxy-4-aza-5α-androstan-3-one which in turn is converted to the corresponding pyridylthio ester, 17β(2-pyridylthiocarbonyl)-4-aza-5α-androstan-3-one, X followed by treatment of the ester with an amine of formula $R^2$-$NH_2$ wherein $R^2$ is as defined hereinabove to form a 17β(N-$R^2$-carbamoyl)-4-aza-5α-androstone-3-one XI which is dehydrogenated as previously described to produce compound XIV, 17β-(N-$R^2$-carbamoyl)-4-aza-androst-1-en-3-one.

In another alternate method of introducing the 17β-(N-$R^2$-carbamoyl)substituent into a 17β-carboxy androstane compound of formula VI, XII or IX, each is treated in a manner similar to the procedure described in *Steroids*, Vol. 35 #3, Mar. 1980, p. 1–7 with dicyclohexylcarbodiimide and 1-hydroxybenzotriazole to form the 17β-(1-benzotriazoloxycarbonyl)-4-aza-5α-androst-1-en-3-one, VII, XIII or X, wherein X is 1-benzotriazoloxy or 17β-(1-benzotriazoloxy-carbonyl)-4-aza-5α-androstan-3-one, X.

The above reactions are schematically represented in the following structural formula outline.

X is pyridylthio or 1-benzotrizoloxy

The compounds of the present invention, prepared in accordance with the method described above, are, as already described, potent anti-androgens by virtue of their ability to specifically inhibit testosterone-5α-reductase.

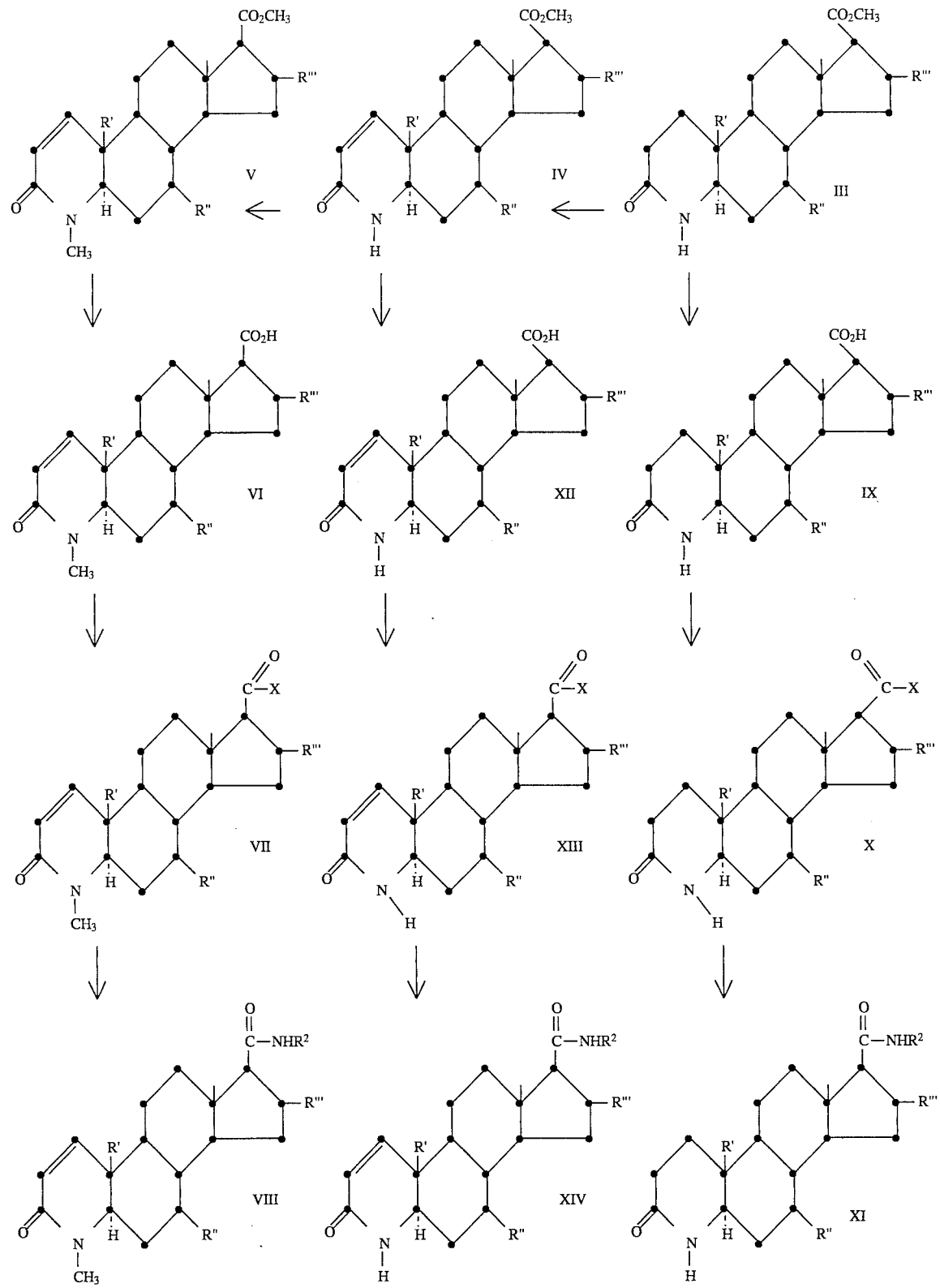

Accordingly, the present invention is particularly concerned with providing a method of treating the hyperandrogenic conditions of androgenic alopecia, including male pattern alopecia, acne vulgaris, seborrhea, and female hirsutism by topical administration, and a method of treating all of the above conditions as well as benign prostatic hypertrophy, by systemic administration, of the novel compounds of the present invention.

The present invention is thus also concerned with providing suitable topical and systemic pharmaceutical formulations for use in the novel methods of treatment of the present invention.

The compositions containing the compounds of the present invention as the active ingredient for use in the treatment of benign prostatic hypertrophy can be administered in a wide variety of therapeutic dosage forms in conventional vehicles for systemic administration, as, for example, by oral administration in the form of tablets, capsules, solutions, or suspensions, of by intravenous injection. The daily dosage of the products may be varied over a wide range varying from 5 to 2,000 mg, preferably from 5 to 200 mg.

The compositions are preferably provided in the form of scored tablets containing 5, 10, 25, 50, 100, 150, 250, and 500 milligrams of the active ingredient for the symptomatic adjustment of the dosage to the patient to be treated. An effective amount of the drug is ordinarily supplied at a dosage level of from about 0.1 mg. to about 50 mg./kg. of body weight per day. Preferably the range is from about 0.1 mg. to 7 mg./kgs. of body weight per day and more preferably from about 0.1 to about 3 mg/kg of body weight per day. These dosages are well below the toxic dose of the product. Capsules containing the product of this invention can be prepared by mixing an active compound of the present invention with lactose and magnesium stearate, calcium stearate, starch, talc, or other carriers, and placing the mixture in gelatin capsule. Tablets may be prepared by mixing the active ingredient with conventional tableting ingredients such as calcium phosphate, lactose, corn starch or magnesium stearate. The liquid forms in suitably flavored suspending or dispersing agents such as the synthetic and natural gums, for example, tragacanth, acacia, methylcellulose and the like. Other dispersing agents which may be employed include glycerin and the like. For parenteral administration, sterile suspensions and solutions are desired. Isotonic preparations which generally contain suitable preservative are employed when intravenous administration is desired.

For the treatment of androgenic alopecia, including male pattern alopecia, acne vulgaris, seborrhea, female hirsutism, the compounds of the present invention are administered in the form of a pharmaceutical composition comprising the active compound in combination with a pharmacologically acceptable carrier adapted for topical administration. These topical pharmaceutical compositions may be in the form of a solution, cream, ointment, gel, lotion, shampoo or aerosol formulation adapted for application to the skin. These topical pharmaceutical compositions containing the compounds of the present invention ordinarily include about 0.1% to 15%, preferably about 0.1 to5%, and more preferably about 0.1% to. 2%, of the active compound, in admixture with a pharmaceutically acceptable carrier.

The method of preparing the novel compounds and compositions of the present invention, already described above in general terms, may be further illustrated by the following examples.

EXAMPLE 1

Methyl 3-oxo-4-aza-5α-androst-1-ene-17β-carboxylate

A suspension of 83.7 g of methyl 3-oxo-4-aza-5α-androstane-17-carboxylate* and 126.5 g of benzeneseleninic anhydride in 2.09 l of chlorobenzene was heated at reflux for 2 hours. The reflux condenser was switched to a distillation head and the mixture was distilled slowly to remove water that had formed in the reaction (2 hours). The solution was evaporated to leave 198 g of wet residue. The residue as a solution in dichloromethane was washed with saturated aqueous NaHCO₃ solution and saturated NaCl solution, then dried and evaporated to leave 172.4 g. This material was chromatographed on 2.56 kg of silica gel eluting first with dichloromethane (5 l) and then with 4:1 dichloromethaneacetone. The desired product eluted after 8 l and amounted to 53.4 g. It was rinsed with diethyl ether and dried to leave 49.5 g, m.p. 278°–280° C. In a similar fashion the following compounds were converted to their corresponding Δ1 derivatives:

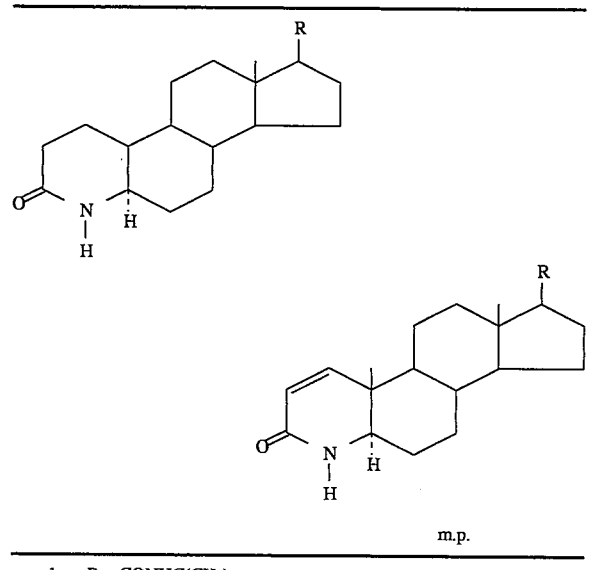

| | | m.p. |
|---|---|---|
| 1a | R = CONHC(CH₃)₃ | 252–254° C. |
| 1b | = CONHC(CH₃)₂CH₂C(CH₃)₃ | 224–226° |

*Rasmusson Johnston and Arth. U.S. Pat. No. 4,377,584, Mar. 22, 1983.

EXAMPLE 2

Methyl 4-methyl-3-oxo-4-aza-5α-androst-1-ene-17β-carboxylate

A suspension of 25 g of the product of Example 1 and 2.25 g of sodium hydride in 500 ml of dry dimethylformamide was stirred under nitrogen for 15 minutes. Methyl iodide (15 ml) was added dropwise and the mixture was stirred for 30 minutes at room temperature. Additional (5 ml) methyl iodide was added and the mixture was heated at 50° C. for 2 hours. After cooling the mixture was diluted with water to 2 l. The solid was separated after cooling and amounted to 25.4 g, m.p. 159°–161° C.

In a similar fashion the following compounds were converted to their corresponding 4-methyl derivatives:

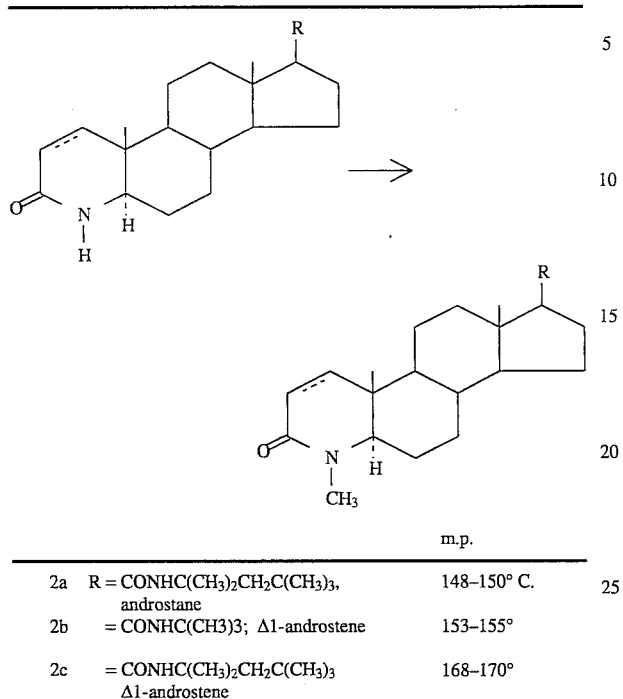

|    |                                      | m.p.       |
|----|--------------------------------------|------------|
| 2a | R = CONHC(CH3)2CH2C(CH3)3, androstane | 148–150° C. |
| 2b | = CONHC(CH3)3; Δ1-androstene         | 153–155°   |
| 2c | = CONHC(CH3)2CH2C(CH3)3 Δ1-androstene | 168–170°   |

EXAMPLE 3

S-(2-Pyridyl) 4-methyl-3-oxo-4-aza-5α-androst-1-ene-17β-thiocarboxylate

A suspension of 25 g of the product of Step in 125 ml of methanol was treated with a solution of KOH (*12.5 g) in 12.5 ml of water. After refluxing for 4 hours, the solution was acidified with 6 NHCl and then was diluted with water. The crude acid (23.32 g) was separated, dried and had m.p. 300° C.

The crude, dry acid (23 g), triphenylphosphine (36.45 g) and 2,2'-dipyridyldisulfide (30.4 g) were suspended in 138 ml of toluene with stirring for 3 hours at room temperature. The reaction mixture was directly chromatographed on a column of 4.5 kg of silica gel eluting with 9:1 ethyl acetate-acetone to give 20.4 g of the desired product, m.p. 218°–220° C.

Continued elution with acetone gave 5.2 g of the methanol addition product, S-(2-pyridyl) 1α-methoxy-4-methyl-3-oxo-4-aza-5α-androstane-17β-thio-carboxylate, m.p. 221°–223° C. as a by-product.

3A. In a similar fashion the product of Example 1 was converted into S-(2-pyridyl) 3-oxo-4-aza-5α-androst-1-ene-17β-thiocarboxylate, m.p. 230°–232° C.

3B. In a similar manner methyl 3-oxo-4-aza-5α-androstane 17-carboxylate was converted into S-(2-pyridyl) 3-oxo-4-aza-5α-androstane-7β-thiocarboxylate, m.p. 232°–234° C.

EXAMPLE 4

N-t-butyl 4-methyl-3-oxo-4-aza-5α-androst-1-ene-17β-carboxamide, m.p. 152°–154° C.

Anhydrous et-butylamine was bubbled for 30 added into a suspension of 2.5 g of the pyridylthioester of Example 3 in 70 ml of tetrahydrofuran. After 60 minutes exposure, the resulting solution was evaporated and the residue was chromatographed on 125 g of silica gel. Elution with 20:1 ethyl acetate dichloromethane afforded 1.5 g of the product, m.p. 152°–154° C.

When the example is repeated using an appropriate amine and an appropriate pyridylthioester, the following products were obtained:

4b: N-t-butyl 3-oxo-4-aza-5α-androstane-17β-carboxamide, m.p. 275°–276° C.

4c: N-(2,4,4-trimethyl-2-pentyl) 4-methyl-3-oxo-4-aza-5α-androst-1-ene-17β-carboxamide, m.p. 168°–170° C.

EXAMPLE 5

5-Oxo-3,5-secoetian-3,20-dioic acid

To a solution of 200 g of 3-oxo-4-etien-20-oic acid in 3.5 l of t-butanol at 80° was added a solution of 198.4 g of sodium carbonate in 474 ml of water. A warm (65° C.) solution of 948.5 g of sodium metaperiodate and 6.95 g of permanganate in 3.5 l of water was added at such a rate that the reaction mixture was maintained at 80° C. After addition the mixture was heated at reflux for one hour. The mixture stood at room temperature overnight. The inorganic salts were removed by filtration and the cake was washed with 225 ml of water. A solution of 5% aqueous sodium bisulfite was added to reduce the iodine that was present. The t-butanol was removed under reduced pressure and the aqueous residue was acidified with conc. hydrochloric acid. The separated gum was extracted into dichloromethane and was washed with 5% aqueous sodium bisulfite, saturated sodium chloride solution, then dried and concentrated to an off-white residue (214 g). Crystalline material was obtained by suspending the residue in ether and diluting with hexane to give 152 g, m.p. 189°–192° C.

EXAMPLE 5B

3-Oxo-4-aza-5-etien-20-oic acid

A suspension of 64.7 g of the dioic acid of Step 5 in 350 ml of ethylene glycol was treated with 80 ml of liquid ammonia. The resulting solution was heated at a rate of 3°/min. up to 180° C. and was held at that temperature for 15 minutes. After cooling, 1 liter of water was added and the mixture was acidified with 10% hydrochloric acid to a pH of 1.5. The product was removed and washed with water, then air dried to leave 57.5 g of the product, m.p. 310° C.

EXAMPLE 5C

3-Oxo-4-aza-5α-etian-20-oic acid

A solution of 136 g of the Δ5-acid of Example 5B in 16.32 ml of acetic acid was hydrogenated at 60° C. in the presence of platinum catalyst (from 16.32 g of $PtO_2$) at 40 psig for 3 hours. The catalyst was removed and the solution concentrated to give 128.2 g of crude product. The material was washed well with 3 l of water then filtered an air dried to leave 125 g of the white solid, m.p. 310°.

This material is also obtained by saponification of methyl 3-oxo-4-aza-5α-androstane-17β-carboxylate (methyl 3-oxo-4-aza-5α-etien-20-oate) in 7% methanolic potassium hydroxide followed by an acidic work-up.

EXAMPLE 5D

N-(2,4,4-trimethyl-2-pentyl)
3-oxo-4-aza-5α-androstane-17β-carboxamide

A solution of 5.0 g of the product of Example 5C, 3.35 g of dicyclohexylcarbodiimide and 3.18 g of 1-hydroxybenztriazole in 500 ml of dichloromethane was stirred at room temperature overnight. The solid was separated by filtration and the filtrate was treated with 2,4,4-trimethyl-2-pentylamine (t-octylamine). This solution stood at room temperature for 64 hours. A small amount of solid was removed and the solution was washed successively with 10% aqueous sodium hydroxide, water, 10% hydrochloric acid and saturated aqueous sodium chloride. After drying and concentration the crude product was eluted through 240 g of silica gel with 3:7 acetone-dichloromethane to give 5.5 g of the product, m.p. 250°–251° C.

EXAMPLE 5E

Example 5D is repeated using t-butylamine in place of 2,2,4-trimethyl-2-pentylamine to obtain N-t-butyl 3-oxo-4-aza-5α-androstane-17β-carboxamide, m.p. 274°–276° C.

EXAMPLE 6
Alcoholic Solution

| | |
|---|---|
| 17β-(N-tertbutylcarbamoyl)-4-aza-5α-androst-1-en-3-one | 15.0% by weight |
| Water | 45 |
| Ethyl Alcohol | 40 |

EXAMPLE 7
Topical Cleanser

| | |
|---|---|
| 17β-(N-tertbutylcarbamoyl)-4-aza-5α-androst-1-en-3-one | 10.00% by weight |
| Water | 70.439 |
| Chamomile | 0.01 |
| Aloe vera gel | 0.01 |
| Allantoin | 0.001 |
| Triethanolomine | 0.02 |
| METHOCEL ® 40-100 (Dow) | 1.50 |
| Glycerine | 3.00 |
| Sodium lauryl sulfate | 15.00 |
| Vitamin A Oil | 0.01 |
| Vitamin E Oil | 0.01 |

EXAMPLE 8
Cleansing Cream

| | |
|---|---|
| 17β-(N-tertbutylcarbamoyl)-4-aza-5α-androst-1-en-3-one | 5.0% by weight |
| Synthetic beeswax | 14.0 |
| PPG2 Myristyl propionate | 5.0 |
| Lanolin Alcohol | 0.5 |
| Mineral Oil | 36.0 |
| Propyl Paraben | 0.15 |
| Sodium Borate | 1.0 |
| Water | 38.35 |

EXAMPLE 9
Skin Gel

| | |
|---|---|
| 17β-(N-tertbutylcarbamoyl)-4-aza-5α-androst-1-en-3-one | 2.00% by weight |
| PPG2 Myristyl Ether Propionate | 45.00 |
| PPG10 Cetyl Ether | 5.00 |
| C18–C36 Triglyceride | 4.00 |
| Myristyl Myristate | 3.00 |
| Glyceryl Tribebenate | 2.00 |
| Cyclomethicone | 34.00 |
| Polyethylene | 5.00 |

EXAMPLE 10
Skin Lotion

| | |
|---|---|
| 17β-(N-tertbutylcarbamoyl)-4-aza-5α-androst-1-en-3-one | 1.0% by weight |
| DEA Oleth 3 Phosphate | 1.0 |
| Emulsifying Wax | 2.0 |
| C18–C36 Wax Fatty Acids | 1.0 |
| PPG2 Myristyl Propionate | 5.0 |
| Glycerine | 3.0 |
| Triethanolamine | 0.5 |
| Water | 86.5 |

EXAMPLE 11
Shampoo Gel

| | |
|---|---|
| 17β-(N-tertbutylcarbamoyl)-4-aza-5α-androst-1-en-3-one | 2.0% by weight |
| Isopropanolamine Lauryl Sulfate | 81.5 |
| Cocoamide DEA | 8.0 |
| C18–C36 Wax Acid Glyceryl Ester | 4.5 |
| PPG5 Ceteth 10 Phosphate | 4.0 |

EXAMPLE 12
Cream Shampoo

| | |
|---|---|
| 17β-(N-tertbutylcarbamoyl)-4-aza-5α-androst-1-en-3-one | 0.1% by weight |
| Sodium Laureth Sulfate | 65.0 |
| Glyceryl Tribebenate | 2.0 |
| Hydrolysed Collagen | 1.0 |
| Lauric Diethanolamide | 5.0 |
| Water | 26.9 |

What is claimed is:

1. A method of treating androgenic alopecia which comprises orally administering to a human in need of such treatment a therapeutically effective amount of 17β-(N-tertbutylcarbamoyl)-4-aza-5α-androst-1-en-3-one.

2. The method of claim 1 wherein the androgenic alopecia is male pattern alopecia.

\* \* \* \* \*

UNITED STATES PATENT AND TRADEMARK OFFICE
CERTIFICATE OF CORRECTION

PATENT NO. : 5,571,817
DATED : November 5, 1996
INVENTOR(S) : Gary H. Rasmusson et al.

It is certified that error appears in the above-indentified patent and that said Letters Patent is hereby corrected as shown below:

On the title page, item [54] and column 1, the title of the invention should read --METHODS OF TREATING ANDROGENIC ALOPECIA WITH FINASTERIDE--.

Signed and Sealed this

Eleventh Day of March, 1997

Attest:

BRUCE LEHMAN

Attesting Officer

Commissioner of Patents and Trademarks